United States Patent
Brown et al.

(10) Patent No.: US 10,039,848 B2
(45) Date of Patent: Aug. 7, 2018

(54) REUSABLE PORTABLE DECONTAMINATION SYSTEM FOR TRANSPORTATION ASSETS

(71) Applicant: AEROCLAVE, LLC, Winter Park, FL (US)

(72) Inventors: Ronald D. Brown, Maitland, FL (US); Paul M. Gray, Ocoee, FL (US); James S. Amrhein, Oviedo, FL (US)

(73) Assignee: Aeroclave, LLC, Winter Park, FL (US)

( * ) Notice: Subject to any disclaimer, the term of this patent is extended or adjusted under 35 U.S.C. 154(b) by 243 days.

(21) Appl. No.: 14/747,195

(22) Filed: Jun. 23, 2015

(65) Prior Publication Data

US 2016/0166721 A1    Jun. 16, 2016

Related U.S. Application Data

(60) Provisional application No. 62/015,681, filed on Jun. 23, 2014.

(51) Int. Cl.
| | | |
|---|---|---|
| *A61L 2/07* | (2006.01) | |
| *A61L 2/20* | (2006.01) | |
| *A61L 2/24* | (2006.01) | |

(52) U.S. Cl.
CPC ............... *A61L 2/07* (2013.01); *A61L 2/20* (2013.01); *A61L 2/24* (2013.01)

(58) Field of Classification Search
CPC .............. A61L 2/07; A61L 2/20; A61L 2/24
See application file for complete search history.

(56) References Cited

U.S. PATENT DOCUMENTS

| | | | | |
|---|---|---|---|---|
| 3,295,471 A | * | 1/1967 | Cook | A47F 5/13 108/163 |
| 4,922,626 A | * | 5/1990 | Fiddler | F26B 21/083 34/80 |
| 6,564,699 B1 | * | 5/2003 | Vincente | A21C 13/00 165/267 |
| 7,901,618 B2 | | 3/2011 | McVey et al. | |
| 8,128,888 B2 | | 3/2012 | Bacik et al. | |
| 2005/0074359 A1 | | 4/2005 | Krieger et al. | |

(Continued)

FOREIGN PATENT DOCUMENTS

WO    2008/104085    9/2008

*Primary Examiner* — Sean E Conley
(74) *Attorney, Agent, or Firm* — Beusse, Wolter, Sanks & Maire, PLLC; Robert L. Wolter

(57) ABSTRACT

A reusable portable decontamination system is provided for a transportation asset. The decontamination system includes a plurality of insulated panels detachably secured together to form an enclosure for the transportation asset and other equipment. The decontamination system also includes a humidifying module in fluid communication with an interior of the enclosure to raise a temperature and a humidity of the interior of the enclosure to a predetermined temperature level and a predetermined humidity level for a timed duration. Additionally, the decontamination system includes a dehumidifying module in fluid communication with the interior of the enclosure to lower the temperature and the humidity of the interior of the enclosure from the predetermined temperature level and the predetermined humidity level to ambient levels. A storage and decontamination module is also presented, to decontaminate one or more components of a transportation asset.

17 Claims, 8 Drawing Sheets

(56) References Cited

U.S. PATENT DOCUMENTS

2005/0260096 A1\* 11/2005 Voyten ..................... A61L 2/12
  422/21
2016/0030264 A1\* 2/2016 Lehmann ............ A61M 16/161
  600/22

\* cited by examiner

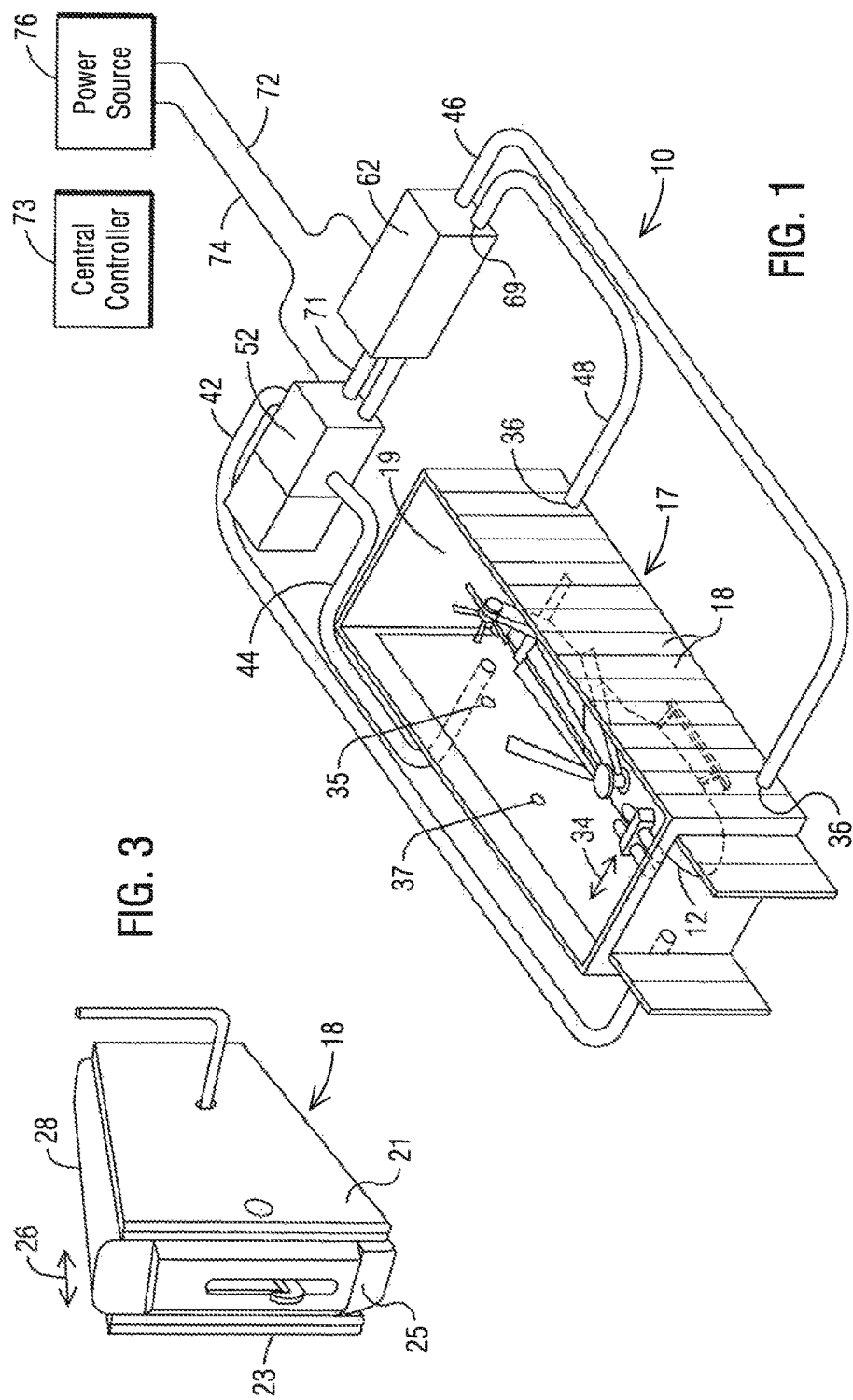

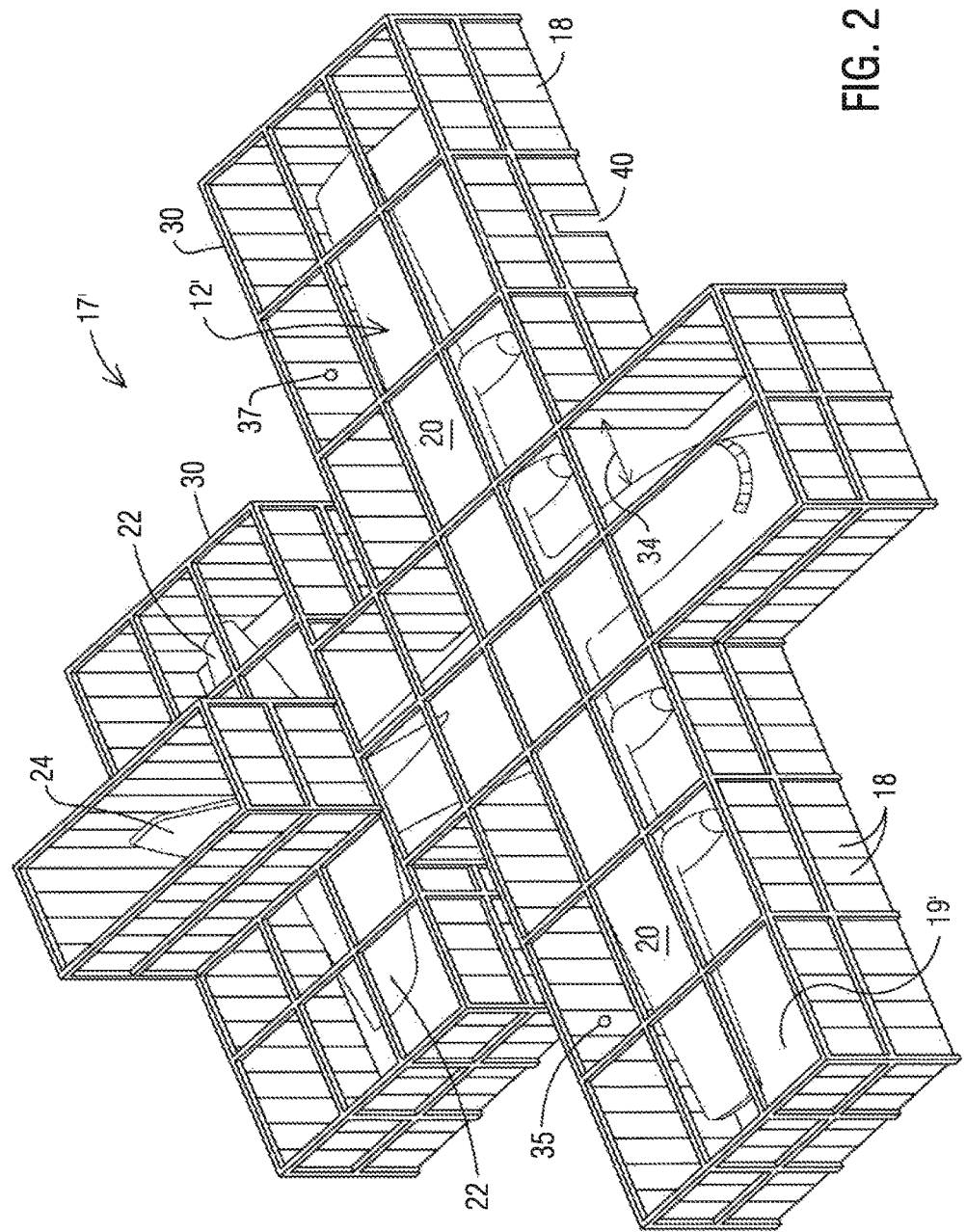

REUSABLE PORTABLE DECONTAMINATION SYSTEM FOR TRANSPORTATION ASSETS

CROSS-REFERENCE TO RELATED APPLICATIONS

This application claims benefit to Provisional Application No. 62/015,681, filed Jun. 23, 2014, the entire contents of which are hereby incorporated by reference as if fully set forth herein, under 35 U.S.C. § 119(e).

STATEMENT OF GOVERNMENT INTEREST

This invention was made with government support under Contract No. FA865014C6518 awarded by the Department of Defense. The government has certain rights in the invention.

BACKGROUND OF THE INVENTION

Several types of decontamination systems employing various decontamination methods have been developed to decontaminate transportation assets such as, for example, vehicles, fixed and rotary wing aircraft and rail cars, etc. However, these decontamination systems do not have the capability to effectively decontaminate an interior and exterior of a transportation asset, without requiring personnel protective equipment. For example, hot soapy water (HSW) is a decontamination method that can be used to partially decontaminate an exterior of a transportation asset, but is not feasible to decontaminate an interior of the transportation asset.

Biothermal decontamination systems may define a chamber and manipulate the environment within the chamber in a manner that is effective to render the decontaminants safe and/or more susceptible to additional decontamination treatment. Such manipulation may include raising a temperature and/or a humidity level in the chamber to threshold levels for set periods of time. During biothermal decontamination, biological agents within the chamber are neutralized by the combination of raised temperature and raised humidity for the set period of time. However, these biothermal decontamination systems cannot uniformly control the temperature and humidity over the interior and exterior of transportation assets. Consequently, there remains room in the art for improvement.

In certain circumstances, portable decontamination systems are needed, to decontaminate a transportation asset at a remote location, where the decontamination system can be transported and built on site. For example, transportation assets used in warfare may encounter chemical or biological agents in remote locations, and thus require decontamination at these remote locations. However, conventional decontamination systems are bulky and thus are not easily transportable.

BRIEF DESCRIPTION OF THE INVENTION

The present invention relates to decontamination systems that use bio-thermal decontamination methods. More specifically, the invention relates to such systems that are portable and are used for decontamination of transportation assets, as well as other types of equipment.

The invention disclosed herein may be particularly useful for decontaminating spaces and surfaces of transportation assets, such as aircrafts, that are frequently exposed to harmful viruses, bacteria, chemicals, etc. Although conventional decontamination systems have been developed for transportation assets, these systems are either limited to decontamination of a portion of the transportation asset or are confined to use at a single decontamination site. The invention disclosed herein overcomes these noticeable drawbacks of conventional decontamination systems.

BRIEF DESCRIPTION OF THE DRAWINGS

FIG. 1 is a top perspective view of a reusable portable decontamination system for a transportation asset in accordance with aspects of embodiments of the invention.

FIG. 2 is a top perspective view of an alternate enclosure of the reusable portable decontamination system of FIG. 1.

FIG. 3 is a side perspective view of an insulated panel used to form the enclosure of the portable decontamination system of FIG. 1.

DETAILED DESCRIPTION OF THE INVENTION

Figure 4A:
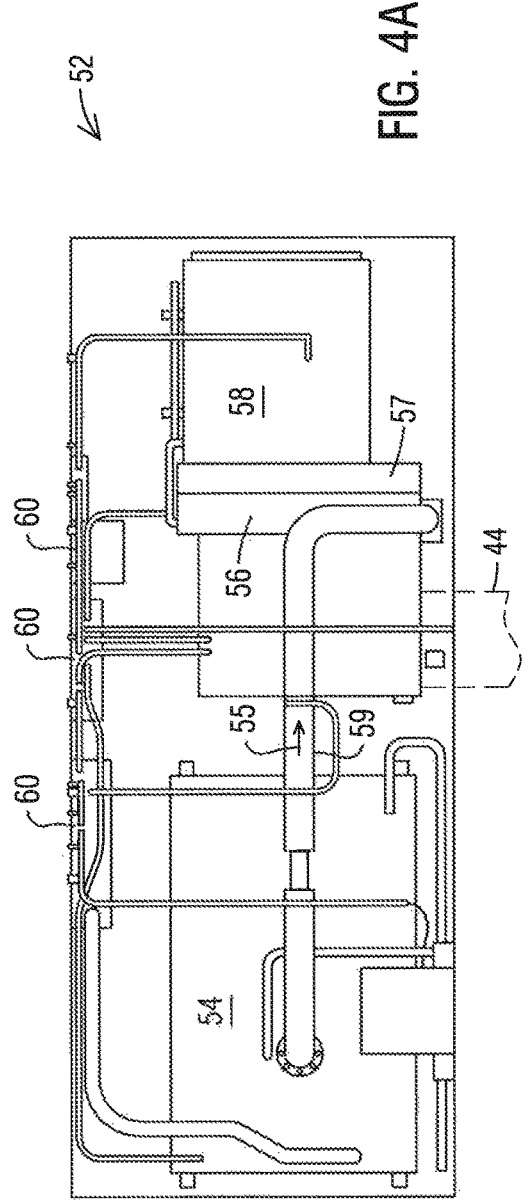
FIGS. 4A and 4B are respective top and side views of an interior of a humidifying module of the portable decontamination system of FIG. 1.

A more particular description of the invention briefly described above will be rendered by reference to specific embodiments thereof that are illustrated in the appended drawings. Understanding that these drawings depict only typical embodiments of the invention and are not therefore to be considered to be limiting of its scope, the invention will be described and explained.

FIG. 1 illustrates a reusable portable decontamination system 10 for bio-thermal decontamination of an interior and exterior of a transportation asset, such as an aircraft 12. In the exemplary embodiment of FIG. 1, the aircraft 12 is a helicopter. The system 10 includes a humidifying module 52 and a dehumidifying module 62 which can be transported to the site of the aircraft 12 using various transportation modes such as air, rail or ground transportation. Additionally, a storage/decontamination module 77 (FIGS. 9A, 9B) may be included in the system 10 and is transported with the other modules to the site of the aircraft 12. The system 10 may also include a power source 76 to power the modules 52, 62. The power source 76 includes the necessary power generation components to power the modules 52, 62 through cables 72, 74. In one embodiment, the power source 76 is a local power source at the site of the aircraft 12, such as a generator or local power grid, for example. In another embodiment, the power source 76 is a transportable module that is transported to the site of the aircraft 12 along with the other modules 52, 62, 77. As will be described in more detail below, the humidifying module 52 may include a shipping container within which is housed the necessary components to generate sufficient heat and moisture for a decontamination operation of the aircraft 12. Similarly, the dehumidifying module 62 includes a shipping container within which the necessary components are housed for a dehumidification operation of the aircraft 12. In an exemplary embodiment, the modules 52, 62, 77 of the system 10 may be housed in a single shipping container, such as a 20' International Organization for Standardization (ISO) shipping container or a CONEX box, for example. However, the system 10 is not limited to transportation within any one type of shipping container, and may be shipped in more than one shipping container, for example.

As further illustrated in FIG. 1, the system 10 includes a plurality of insulated panels 18 that are detachably secured together to form an enclosure 17, such that the enclosure 17 has an interior 19 that conforms to a shape of the aircraft 12. By conforming the enclosure 17 to the aircraft 12 shape, the required interior 19 volume, including the transportation asset undergoing heating and cooling during the decontamination process is minimized, thereby maximizing the efficiency of the system 10. However, enclosure conformality is not required for use of the system. As further illustrated in FIG. 1, the insulated panels 18 are secured together such that the enclosure interior 19 provides a minimum clearance 34 between the aircraft 12 and the enclosure 17, to facilitate airflow circulation within the enclosure interior 19. In an exemplary embodiment, the minimum clearance 34 may be in a range of 4-6 feet, for example. In addition to the sides and the roof of the enclosure 17, the insulated panels 18 may be secured together to form a floor of the enclosure 17, to prevent heat loss through the floor of the enclosure 17, during the decontamination process. In an exemplary embodiment, the insulated panels 18 forming the floor may be secured together around wheels or other means of supporting a weight the aircraft 12, such that the weight of the aircraft 12 is not imposed on the insulated panels 18. After decontamination of the aircraft 12 is complete, the insulated panels 18 are detached from one another and transported to the site of another aircraft requiring decontamination. Although FIG. 1 depicts that the enclosure 17 is formed by detachably securing the insulated panels 18 together, the enclosure 17 is not limited to this structural arrangement and may be formed by any means for constructing a portable enclosure, as appreciated by one skilled in the art. Additionally, the enclosure 17 is not limited to a portable enclosure and may be a fixed enclosure at the site location, for example.

FIG. 2 illustrates an alternate enclosure 17' formed with the insulated panels 18 to conform to a shape of an aircraft 12', such as an airplane, for example. In an exemplary embodiment, the aircraft 12' is a C-130 aircraft, for example. As illustrated in FIG. 2, the enclosure 17' may include one or more doors 40, for access to the enclosure interior 19'. As shown in FIG. 2, the insulated panels 18 of the enclosure 17' are secured together in such a manner so that the interior 19' provides the minimum clearance 34 between various parts of the aircraft 12' and the enclosure 17', including the wings 20, the tail 22 and the rudder 24 of the aircraft 12'.

As illustrated in FIG. 3, each insulated panel 18 of the enclosure 17 includes a pair of sheets 21, 23 with an insulating foam layer 25 of a thickness 26 there between. In an exemplary embodiment, the insulating foam layer 25 may be expanded polystyrene, polyurethane or other insulating material. In an exemplary embodiment, the thickness 26 of the panel 18 may be in a range of 4-6 inches, the width of the panel 18 is in a range of 44-52 inches, such as 48 inches, and the length of the panel 18 is adjusted to a height of the enclosure 17, based on the type of aircraft 12. In an exemplary embodiment, the R-value of the layer 25 may be in a range of 20-28. The sheets 21, 23 may be made of any metallic, wood or wood composite material, such as powder coated galvanized metal, for example. As further illustrated in FIG. 3, the insulated panels 18 of the enclosure 17 include a tongue and groove interlocking mechanism 28, to detachably secure the insulated panels 18 together. However, any type of interlocking mechanism known to one skilled in the art may be used to detachably secure the insulated panels 18 together, such as a cam lock interlocking mechanism, for example. The interlocking mechanism 28 allows the panels 18 to be detachably secured together and taken apart, with minimal use of tools, in order to facilitate the mobility of the system 10.

Again in reference to FIG. 1, the portable decontamination system 10 includes insulated ducts 42, 44 that provide fluid flow communication between the humidifying module 52 and the enclosure interior 19 and insulated ducts 46, 48 that provide fluid flow communication between the dehumidifying module 62 and the enclosure interior 19. In an exemplary embodiment, the ducts 42, 44, 46, 48 are 20"-24" round flexible ducts made of insulation material, for example. The insulated panels 18 are arranged to form the enclosure 17 and the insulated ducts 42, 44, 46, 48 are connected to the humidifying module 52 and the dehumidifying module 62 using fixtures. The insulated panels 18 may be prefabricated to include openings 36 for connection of the ducts 42, 44, 46, 48. An inventory of the insulated panels 18 may be performed, such that a particular set of insulated panels 18 may correspond to a particular model of a transportation asset and the insulated panels 18 may be arranged in a particular order so that a subset of the insulated panels 18 that form the openings 36 are consistently positioned from transportation asset to transportation asset of the particular model. In an exemplary embodiment, any gap between the openings 36 and the ducts 42, 44 may be sealed, to prevent unwanted heat/air loss, for example.

The humidifying module 52 is in fluid communication with the enclosure interior 19, to raise a temperature within the interior 19 to a predetermined temperature level and to raise a humidity within the interior 19 to a predetermined humidity level. In an exemplary embodiment, the predetermined temperature level is in a range of 0-200 degrees F. and predetermined humidity level is in a range of 0-100%. In another exemplary embodiment, the predetermined temperature level is in a range of 160-180 degrees F. and predetermined humidity level is in a range of 80-90%. After the temperature and the humidity of the enclosure interior 19 have reached the predetermined temperature level and the predetermined humidity level, the humidifying module 52 remains in fluid flow communication with the enclosure interior 19, to maintain the temperature at the predetermined temperature level and the humidity at the predetermined humidity level for a timed duration, such as 1-7 days, for example. In another exemplary embodiment, the time duration is in a range of 3-4 days, for example. In an exemplary embodiment, the temperature is maintained at 170 degrees F.±5 degrees F. and the humidity is maintained at 90%±5% for the timed duration. In an exemplary embodiment, the predetermined temperature level and predetermined humidity level are pathogen specific and the lower the predetermined level and predetermined humidity level, the longer the timed duration for decontamination. After the timed duration, the dehumidifying module 62 may be controlled to lower the temperature within the interior 19 from the predetermined temperature level to an ambient temperature and to lower the humidity within the interior 19 from the predetermined humidity level to an ambient humidity.

Figure 4B:
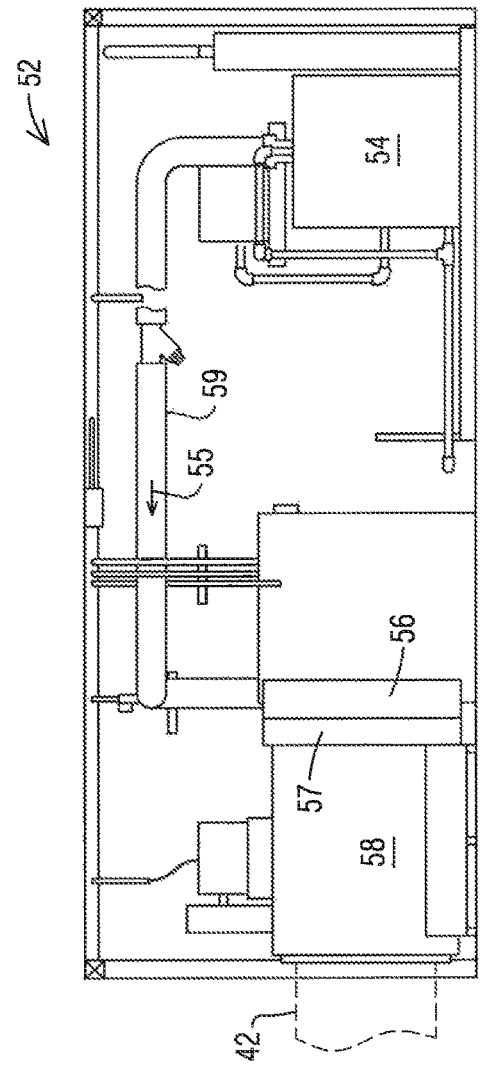

FIGS. 4A-4B illustrate the components of the humidifying module 52. A boiler 54 is provided in the humidifying module 52, to heat water and generate steam 55, which flows to a blower 58 via conduit 59. A dispensing coil 56 at the blower 58 is in fluid communication with the boiler 54, to distribute heat from the steam 55 into surrounding air within a chamber 57. The blower 58 is provided in fluid flow communication with the chamber 57, to direct the heated air from the chamber 57 into the insulated duct 42. Although FIG. 4B depicts the blower 58 connected to one insulated duct 42, the embodiments of the present invention may include a plurality of portals in the humidifying module 52 to connect the blower 58 to multiple insulated ducts that can be used to direct the heated air to the enclosure interior 19. Additionally, in one embodiment, a fixture may be provided, where one side of the fixture is attached to the insulated duct 42 and an opposite side of the fixture is attached to a plurality of insulated ducts, to bifurcate the heated air flow from the insulated duct 42 into the plurality of insulated ducts. In this embodiment, the plurality of insulated ducts may be connected to a plurality of openings along the surface of the enclosure 17, to distribute the heated air flow within the enclosure interior 19, or the insulated ducts may be connected to a plurality of respective enclosures 17, to simultaneously heat more than one enclosure 17. A similar fixture may be provided for the insulated duct 46, to bifurcate the cooled air flow from the insulated duct 46 into a plurality of insulated ducts. As illustrated in FIGS. 1 and 4A, the return insulated duct 44 is provided in fluid communication with the enclosure interior 19, to pass air from the enclosure interior 19 to the chamber 57 within the humidifying module 52. The returned air is then heated by the dispensing coil 56, before it is pushed back out through the duct 42 by the blower 58 and back to the enclosure interior 19. The humidifying module 52 is not limited to the specific structural arrangement of the module 52 depicted in FIGS. 4A-4B and encompasses any means for generating heated air known to one skilled in the art, for purposes of increasing the temperature and humidity and maintaining the temperature and humidity within the enclosure interior 19 at the predetermined levels.

Figure 5A:
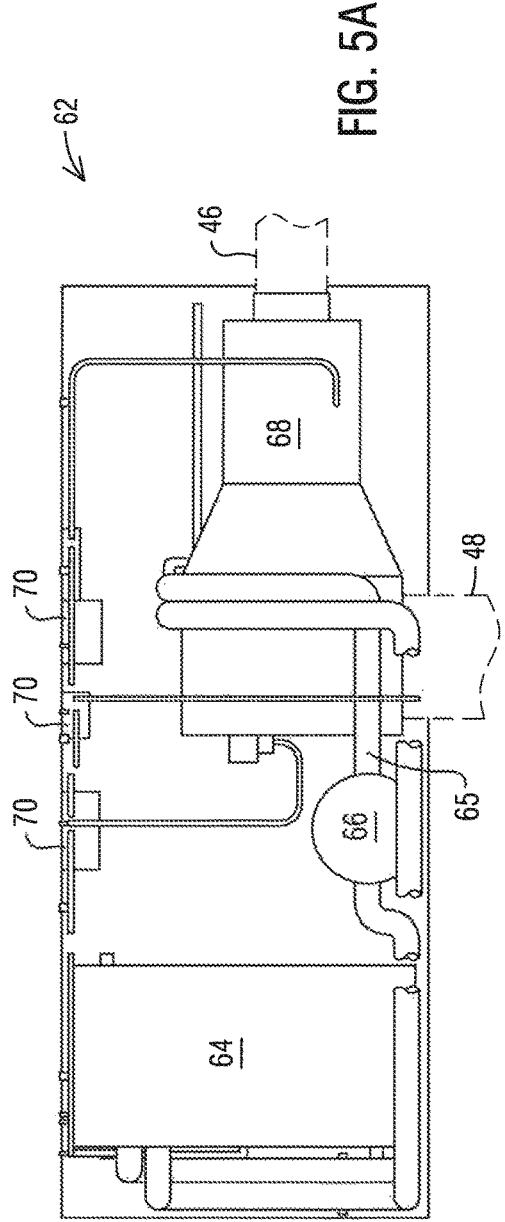
FIGS. 5A and 5B are respective top and side views of an interior of a dehumidifier module of the portable decontamination system of FIG. 1.
Figure 5B:
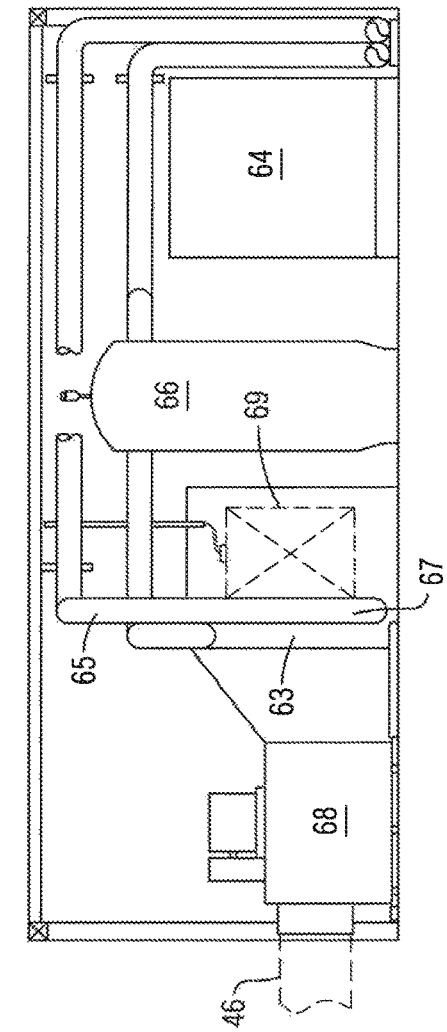

FIGS. 5A-5B illustrate top and side views of the components of the dehumidifying module 62. As discussed above, the dehumidifying module 62 is in fluid communication with the enclosure interior 19, via the insulated duct 46 to direct air from the dehumidifying module 62 to the enclosure interior 19 and the insulated duct 48 to recirculate air from the enclosure interior 19 to the dehumidifying module 62. A chiller 64 is provided, to cool water within the dehumidifying module 62. A coil 67 in fluid communication with the chiller 64 is positioned in a chamber 63, to cool air within the chamber 63 upon receiving chilled water from the chiller 64. When air returns from the enclosure interior 19 through the return insulated duct 48 to the dehumidifying module 62, it passes through an inlet 69, over the coil 67 and to the chamber 63, after which a blower 68 in fluid communication with the coil 67 directs the cooled air back into the insulated duct 46. As illustrated in FIG. 5B, water returned from the coil 67 to the chiller 64 is directed through a pipe 65 that passes through a buffer tank 66, to reduce a temperature of the water before it returns to the chiller 64. The dehumidifying module 62 is not limited to the specific structural arrangement of the module 62 depicted in FIGS. 5A-5B and encompasses any means for generating cooled air known to one skilled in the art, for purposes of reducing the temperature and humidity within the enclosure interior 19 from the predetermined levels to ambient levels.

Figure 6:
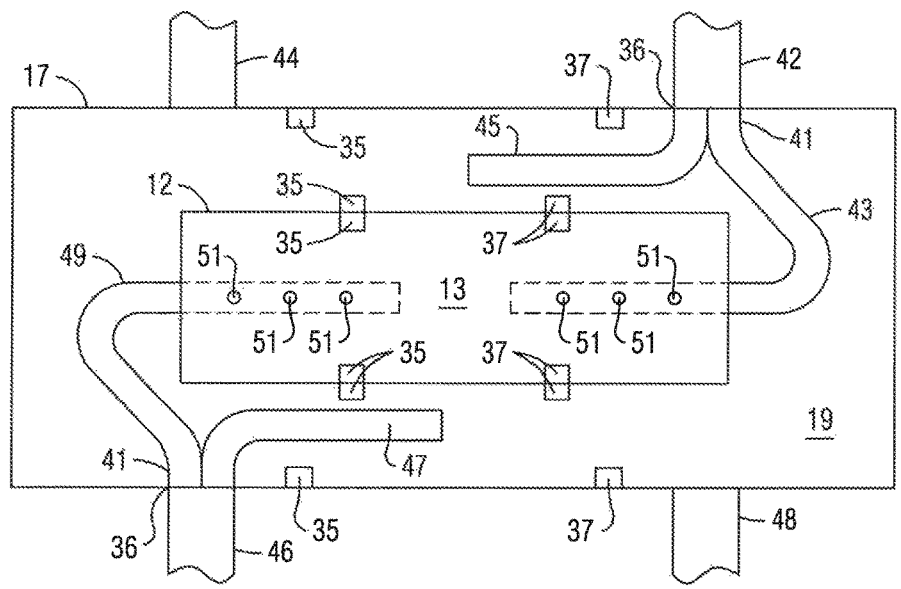
FIG. 6 is a top view of the enclosure of the transportation asset of FIG. 1 with ducting within the interior of the enclosure.

FIG. 6 illustrates a top view of the enclosure 17 of the aircraft 12 of FIG. 1 with ducting within the enclosure interior 19. A fixture 41 is provided within the enclosure interior 19, where one side of the fixture 41 is attached to the insulated duct 42 at the opening 36 and an opposite side of the fixture 41 is attached to a plurality of insulated ducts 43, 45, to bifurcate the heated air flow from the insulated duct 42 into the plurality of insulated ducts 43, 45. A first insulated duct 43 is positioned within an interior 13 of the aircraft 12 and includes openings 51 along a length of the duct 43, to direct heated air into the aircraft interior 13, along a length of the duct 43. Additionally, the insulated duct 43 includes an opening at the end of the duct 43, to further direct heated air within the aircraft interior 13. A second insulated duct 45 is positioned within a region of the enclosure interior 19 that is external to the aircraft 12, to direct heated air within this region of the enclosure interior 19. The insulated duct 45 may include openings along a length of the duct 45, to direct heated air into the interior 19 along a length of the duct 45. As with the insulated duct 43, the insulated duct 45 includes an opening at the end of the duct 45 to direct heated air into the interior 19. As illustrated in FIG. 6, one side of a fixture 41 is also attached to the insulated duct 46 at the opening 36 and an opposite side of the fixture 41 is attached to a plurality of insulated ducts 47, 49, to bifurcate the cooled air from the insulated duct 46 into the plurality of insulated ducts 47, 49. A first insulated duct 49 is positioned within the interior 13 of the aircraft 12 and includes openings 51 along a length of the duct 49, to direct cooled air into the aircraft interior 13, along a length of the duct 49. Additionally, the insulated duct 49 includes an opening at the end of the duct 49, to further direct cooled air within the aircraft interior 13. A second insulated duct 47 is positioned within the region of the enclosure interior 19 that is external to the aircraft 12, to direct cooled air within the region of the enclosure interior 19. The insulated duct 47 may include openings along a length of the duct 47, to direct cooled air into the interior 19 along a length of the duct 47. As with the insulated duct 49, the insulated duct 47 includes an opening at the end of the duct 47 to direct cooled air into the interior 19. Although FIG. 6 depicts that the ducts 43, 49 each extend along a portion of the aircraft interior 13, the ducts 43, 49 may be positioned along an entire length of the aircraft interior 13. Additionally, although FIG. 6 depicts that the airflow is bifurcated at each fixture 41 into a pair of insulated ducts, the airflow may be divided at the fixture 41 into more than two insulated ducts, such that more than one insulated duct may be respectively positioned within the aircraft interior 13 and within the enclosure interior 19. For example, where the aircraft interior 13 includes more than one chamber or passage, more than one insulated duct may be positioned within the aircraft interior 13, such that at least one insulated duct is positioned along the length of each chamber or passage. Additionally, although FIG. 6 depicts one insulated duct 42 to direct heated air and one insulated duct 46 to direct cooled air to the enclosure interior 19, two or more insulated ducts may be respectively used to direct heated air from the humidifying module 52 to different regions of the enclosure interior 19 to more uniformly heat the interior 19 and to direct cooled air from the dehumidifying module 62 to different regions of the enclosure interior 19 to more uniformly cool the interior 19.

As further illustrated in FIG. 6, temperature and humidity sensors 35, 37 are positioned within the enclosure interior 19 and within the aircraft interior 13, to monitor the temperature and humidity within the respective interiors 13, 19. In an exemplary embodiment, the temperature sensors 35 are thermocouples, such as T-type thermocouples (Omega® Part Number 5SRTC-TT-T-20-36) with a dynamic range of 32-662 degrees F. and a tolerance of ±1.8 degrees F. In another exemplary embodiment, thermo-couple grade extension wire is used to connect the sensors 35 with the central controller 73, to preserve the accuracy of the signal from the temperature sensors 35 over distances along the interiors 13, 19. In an exemplary embodiment, the humidity sensors 37 are relative humidity sensors, such as Vaisala® HMT120 Humidity Transmitters with a range of 1-100% relative humidity and an accuracy of ±1.5% at ambient conditions and ±4.0% at high temperature conditions. In an exemplary embodiment, each temperature sensor 35 within the enclosure interior 19 measures an air temperature within the enclosure interior 19 and a temperature of a surface of the enclosure interior 19 where the sensor 35 is mounted. In an exemplary embodiment, each temperature sensor 35 within the aircraft interior 13 measures an air temperature within the aircraft interior 13 and a temperature of a surface of the aircraft interior 13 where the sensor 35 is mounted. As further depicted in FIG. 6, additional temperature and humidity sensors 35, 37 within the enclosure interior 19 are positioned along an exterior surface of the aircraft 12, to measure the temperature and humidity along the exterior surface of the aircraft 12. In an exemplary embodiment, the temperature sensors 35 along the exterior surface of the aircraft 12 measure an air temperature and a temperature of the exterior surface of the aircraft 12 where the sensors 35 are mounted. Although FIG. 6 depicts that two temperature sensors 35 and two humidity sensors 37 are positioned within each of the interiors 13, 19, and two temperature sensors 35 and two humidity sensors 37 are positioned along the exterior surface of the aircraft 12, more than two temperature sensors and more than two humidity sensors may be respectively positioned within the interiors 13, 19 and along the exterior surface of the aircraft 12 and may be positioned at different locations than depicted in FIG. 6.

As illustrated in FIG. 1, a central controller 73 is provided in signal communication with the temperature and humidity sensors 35, 37 positioned within the enclosure interior 19 and aircraft interior 13 that monitor the temperature and humidity within the enclosure interior 19 and aircraft interior 13. As further illustrated in FIGS. 4A-4B, one or more control panels 60 in the humidifying module 52 are connected to the boiler 54 and are also in communication with the central controller 73 to control the operation of the humidifying module 52. In order to commence a decontamination operation of the aircraft 12, a user enters one or more parameters associated with a decontamination mode into the central controller 73, such as the timed duration, the predetermined temperature level, and the predetermined humidity level. The central controller 73 then transmits a signal to the control panels 60, to activate the boiler 54 until the heated air passed through the duct 42 and into the interior 19 causes the temperature to reach the predetermined temperature level and the humidity to reach the predetermined humidity level. In an exemplary embodiment, the temperature at any given time is based on a measured air temperature from the temperature sensors 35 within the interiors 13, 19, a measured surface temperature from the temperature sensors 35, or a combination of air and surface temperature from the temperature sensors 35. In another exemplary embodiment, the temperature at any given time is based on an average of the measured air, surface and/or combined air and surface temperature from the temperature sensors 35 within the interiors 13, 19 and the humidity at any given time is based on an average of the measured humidity from the humidity sensors 37 within the interiors 13, 19. In an embodiment the module 52 may be equipped with an electrical resistance heater to initially heat air introduced into the enclosure interior 19, before steam is injected into the enclosure interior 19, to prevent potential condensation.

During this process, the central controller 73 continuously monitors the temperature and humidity measurements from the sensors 35, 37 in the enclosure interior 19 and the aircraft interior 13. The sensors 35, 37 may be wired or wireless sensors, for example. To that end the temperature of the air at a supply duct and the air at the return duct to the humidifying module to determine a point in time when to initiate a start time of a decontamination mode. As these temperatures converge and are compared to the temperature of the interior of the enclosure and the interior of the aircraft, the timing of the decontamination mode may be initiated when the difference in supply temperature and return temperature are within an acceptable range for a predetermined time and/or the temperature within the enclosure and aircraft is at or within a temperature range for a predetermined time.

After the central controller 73 receives sensor data that the temperature and the humidity measurements within the enclosure interior 19 and the aircraft interior 13 are at the predetermined temperature level and predetermined humidity level, the central controller 73 selectively transmits a signal to the control panels 60, to control the boiler 54, in order to maintain the predetermined temperature level and predetermined humidity level within the enclosure interior 19 and aircraft interior 13 for the timed duration. During the timed duration for decontamination, the central controller 73 continuously monitors the sensors 35, 37 within the enclosure interior 19 and the aircraft interior 13 and selectively transmits the signals to the control panels 60. For example, if the temperature and the humidity fall below the predetermined temperature level and the predetermined humidity level, the central controller 73 transmits a signal to the control panels 60, to control the boiler 54, to increase the temperature and the humidity to the respective predetermined temperature level and predetermined humidity level. Although FIG. 1 depicts that the central controller 73 is positioned external to the modules 52, 62 the embodiments of the present invention may provide that the central controller 73 is positioned in one of the modules 52, 62, for example. In another embodiment, the humidifying module 52 may include an internal controller to independently monitor the temperature and humidity data from the sensors 35, 37 within the enclosure interior 19 and the aircraft interior 13 and activate the boiler 54, for example.

As further illustrated in FIGS. 5A-5B, one or more control panels 70 in the dehumidifying module 62 are connected to the chiller 64 and are also in communication with the central controller 73. After the timed duration associated with decontamination mode has elapsed, the central controller 73 transmits one or more signals to the control panels 70, to activate the chiller 64 until the cooled air passed through the duct 46 and into the enclosure interior 19 and aircraft interior 13 causes the temperature to lower from the predetermined temperature level to an ambient temperature and the humidity to lower from the predetermined humidity level to an ambient humidity within the enclosure interior 19 and aircraft interior 13. During this process, the central controller 73 continuously monitors the sensors 35, 37 within the enclosure interior 19 and aircraft interior 13 and continuously activates the chiller 64, until the temperature and the humidity within the enclosure interior 19 and aircraft interior 13 are at the ambient levels.

In addition, the temperature of air supplied to the enclosure interior 19 and aircraft interior 13 from the dehumidifying module 62 and the temperature of the air returned to the module 62 may be monitored. As these temperatures converge and are compared to the temperature of the interior of the enclosure interior and aircraft interior, the timing of the dehumidifying mode may be initiated when the difference in supply temperature and return temperature are within an acceptable range for a predetermined time and/or the temperature within the enclosure and aircraft is at or within a temperature range for a predetermined time. That is, the dehumidification mode may be held for a predetermined time at a predetermined ambient temperature as well as a predetermined humidity level.

In an exemplary embodiment, the central controller 73 transmits the signals to the control panels 70 over a minimum time period, such that the chiller 64 decreases the temperature and the humidity within the enclosure interior 19 and aircraft interior 13 to the ambient levels over the minimum time period, to prevent condensation from forming over the aircraft 12 interior and exterior surfaces. In one example, the volume of the enclosure interior 19 may be in a range of 10,000-6,000,000 cubic feet and the minimum time period may be in a range of 120-28,800 minutes. When the user wants to commence decontamination of the aircraft 12, the user may enter the minimum time period parameter into the central controller 73, in addition to the other parameters associated with the decontamination mode discussed above. Although FIG. 1 depicts that the central controller 73 is positioned external to the modules 52, 62, in another embodiment the dehumidifying module 62 may include an internal controller to independently monitor the temperature and humidity within the enclosure interior 19 and selectively activate the chiller 64, for example. The internal controller within the dehumidifying module 62 may be in communication with an internal controller within the humidifying module 52 through one or more Ethernet cables 71 (FIG. 1). In this embodiment, the user inputs the parameters of decontamination at the internal controller within the humidifying module 52. The internal controller within the humidifying module 52 then selectively activates the boiler 54, such that the temperature and the humidity within the enclosure interior 19 and aircraft interior 13 is raised to the predetermined temperature level and the predetermined humidity level for the timed duration. The internal controller within the humidifying module 52 then transmits a signal through the Ethernet cables 71 to the internal controller within the dehumidifying module 62, to selectively activate the chiller 64, until the temperature and the humidity within the enclosure interior 19 and aircraft interior 13 is lowered from the predetermined temperature level and the predetermined humidity level to ambient levels over the minimum time period.

Figure 8:
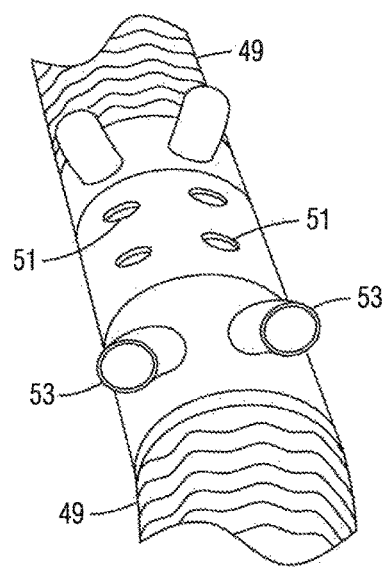
FIG. 8 is a perspective view of an insulated duct of the system of FIG. 7.
Figure 7:
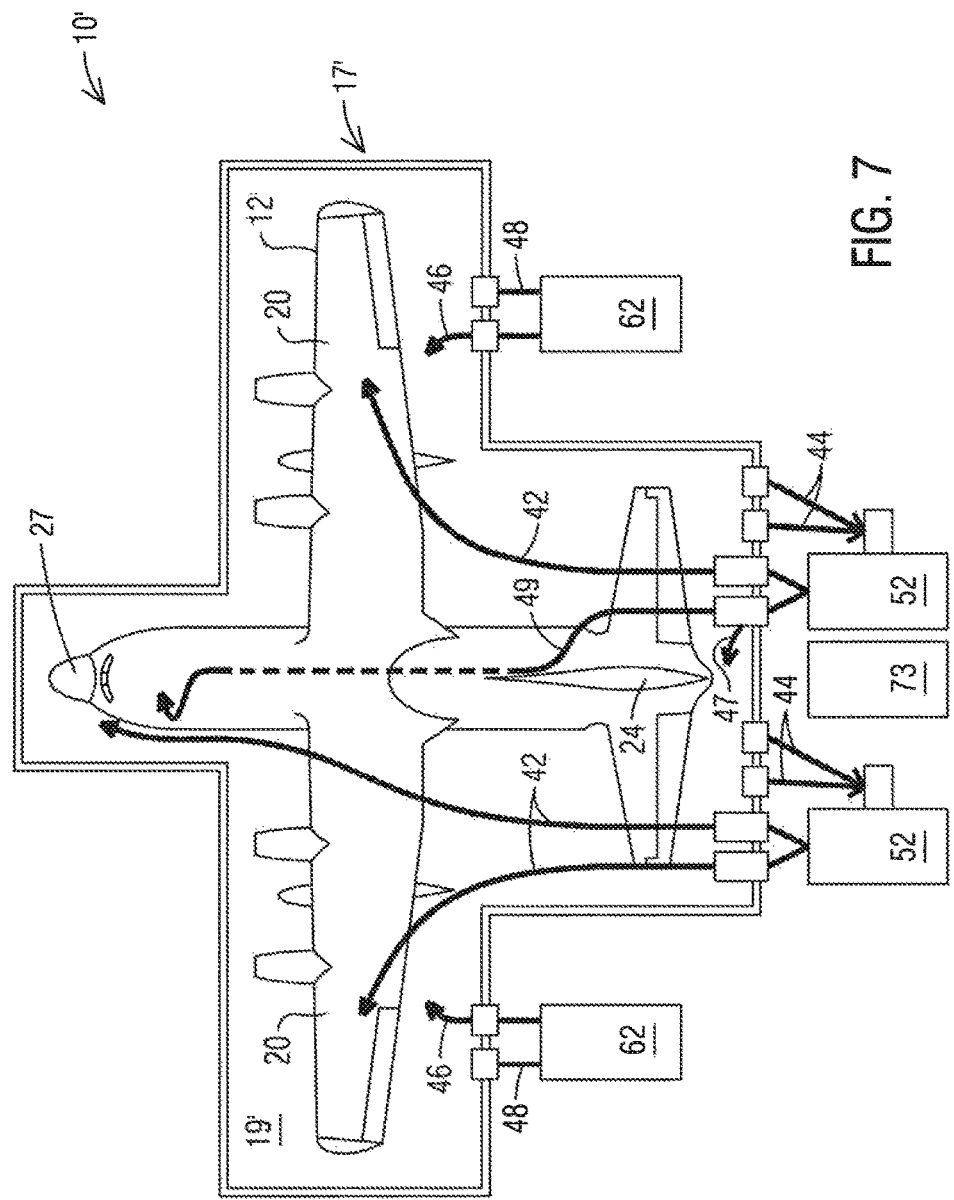
FIG. 7 is a top view of a reusable portable decontamination system for the enclosure of FIG. 2.

FIG. 7 is a top view of a reusable portable decontamination system 10' for the enclosure 17' of FIG. 2. As illustrated in FIG. 7, the system 10' includes two humidifying modules 52, two dehumidifying modules 62 and the central controller 73, which operate in the same manner as discussed above. Temperature and humidity sensors 35, 37 are positioned within different regions of the enclosure interior 19' that are external to the aircraft 12'. Additionally, temperature and humidity sensors 35, 37 are positioned within the aircraft 12' interior and along an exterior surface of the aircraft 12', in a similar manner as discussed above with respect to the temperature and humidity sensors 35, 37 of FIG. 6. As illustrated in FIG. 7, a first humidifying module 52 directs heated air within the enclosure interior 19' with two insulated ducts 42 connected to respective openings in the enclosure 17'. One insulated duct 42 extends within a region of the enclosure interior 19' including a first wing 20 of the aircraft 12' and a second insulated duct 42 extends within a region of the enclosure interior 19' including a nose 27 of the aircraft 12', to direct heated air to these respective regions of the enclosure interior 19', external to the aircraft 12'. A second humidifying module 52 also directs heated air to the enclosure interior 19'. A first insulated duct 42 is connected to an opening in the enclosure 17' and extends within a region of the enclosure interior 19' including a second wing 20 of the aircraft 12' and a second insulated duct is bifurcated into a pair of insulated ducts 47, 49, in the same manner as discussed above with respect to FIG. 6. The first insulated duct 47 extends within a region of the enclosure interior 19' including the rudder 24 of the aircraft 12' to direct heated air to this region of the enclosure interior 19', external to the aircraft 12'. The second insulated duct 49 extends within the aircraft 12' interior, in the same manner as discussed above with respect to FIG. 6. FIG. 8 depicts the second insulated duct 49 positioned within the aircraft 12' interior, including vents 53 positioned within the openings 51, to facilitate the discharge of heated air within the aircraft 12' interior, along the length of the second insulated duct 49. In an exemplary embodiment, the ducts 42 have a 20 inch diameter and the duct 49 has a diameter which reduces from 20" to 12" within an initial region of the aircraft 12' interior, such as the cargo bay, and further reduces from 12" to 8" in a subsequent region of the aircraft 12' interior, such as the flight deck.

As further illustrated in FIG. 7, the system 10' further includes two dehumidifying modules 62 with respective insulated ducts 46, 48 that are used to direct cooled air into different regions of the enclosure interior 19' and reduce the temperature and humidity in the enclosure interior 19' to ambient levels, using the decontamination process previously discussed above. The central controller 73 in the system 10' controls the decontamination process in a similar manner as the central controller 73 discussed above in system 10. During operation of the system 10', the controller 73 receives data from temperature sensors 35 and humidity sensors 37 that are distributed in a plurality of regions of the enclosure interior 19' and aircraft 12' interior. Based on the temperature and humidity data received from each region, the controller 73 may selectively activate one of the two modules 52, or one of the two modules 62, to selectively deliver heated or cooled air to the region. For example, if the central controller 73 determines that temperature sensors 35 within the enclosure interior 19' indicate that the temperature is at the predetermined level but that temperature sensors 35 within the aircraft 12' interior indicate that the temperature in the aircraft 12' interior is less than the predetermined level, the controller 73 may selectively transmit a signal to the second humidifying module 52, such that heated air is selectively delivered through the second insulated duct 49 to the aircraft 12' interior, to increase the temperature in the aircraft 12' interior.

Figure 9A:
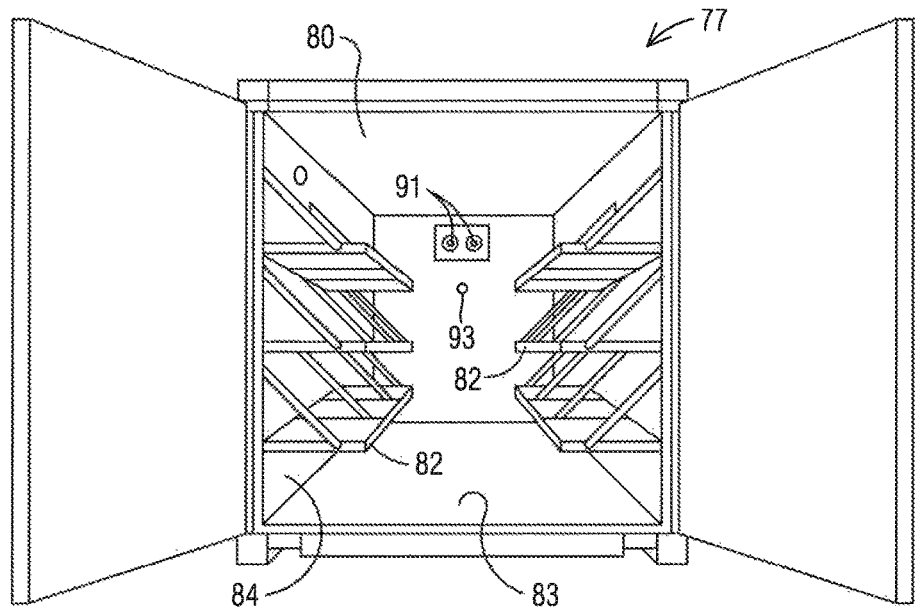
FIGS. 9A and 9B are respective rear and front views of a decontamination module of the portable decontamination system of FIG. 1.
Figure 9B:
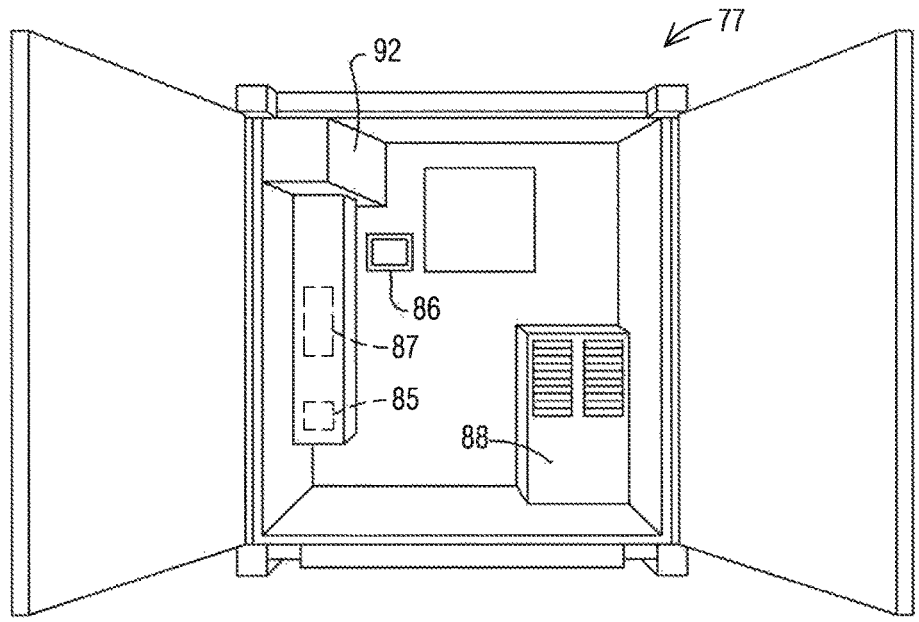

FIGS. 9A-9B illustrate the storage/decontamination module 77 of the portable storage/decontamination system 10. During transport of the system 10 from one aircraft location to another aircraft location, the insulation ducts 42, 44, 46, 48, as well as other duct fixtures or connectors for the panels 18 used to assemble the system 10 may be stored and transported in the storage/decontamination module 77. A decontamination chamber 80 is provided within an interior of the decontamination module 77. During the decontamination of the aircraft 12 by the system 10, the decontamination chamber 80 is used to decontaminate components of the aircraft 12 that may be sensitive to the elevated temperatures and relative humidity associated with bio thermal decontamination. As illustrated in FIG. 9A, one side of the decontamination module 77 includes a plurality of shelves 82 pivotally mounted to an interior surface 84 of the decontamination chamber 80, such that one or more shelves 82 can be pivoted to a horizontal position to hold the aircraft components in the decontamination chamber 80. Alternatively, the transportation asset components may be positioned on the ground 83 of the decontamination chamber 80. As illustrated in FIG. 9B, an opposite side of the decontamination module 77 includes a reservoir 85 in which a disinfectant solution is stored. By way of example, the disinfectant solution may include an aqueous hydrogen peroxide solution that contains about 5% by volume to about 20% by volume of hydrogen peroxide. More preferably, the solution contains about 8% by volume of hydrogen peroxide. The decontamination module 77 also includes a pump 87 in fluid communication with the reservoir 85 and a plurality of nozzles 91 (FIG. 9A) in the decontamination chamber 80.

A programmable controller 86 with a touch-screen is in signal communication with the pump 87 and the reservoir 85 to activate the pump 87 and deliver the disinfectant solution to the nozzles 91 so that the disinfectant solution is dispersed in an atomized form in an interior of the decontamination chamber 80 to decontaminate the aircraft components. The reservoir 85, the pump 87 and the programmable controller 86 can be positioned inside or outside the decontamination chamber 80. The time duration that the disinfectant solution is dispersed through the nozzles 91 may vary according to the volume of the decontamination chamber 80 and the volume of disinfectant solution needed to decontaminate the decontamination chamber 80. To that end, the dispersal of the disinfectant solution through the nozzles 91 may be divided into discrete timed periods including one or more dwell times during which no disinfectant solution is injected interposed between two injection periods. By way of example, an injection may be made continuously for 4 minutes for a first injection period followed by a 2 minute first dwell time, which is then followed by a second 4 minute injection period followed by a second 2 minute dwell time for an injection phase lasting 12 minutes.

After the injection mode has been completed, an aeration mode is initiated by the controller 86 transmitting one or more signals to activate a HVAC system 88. During the aeration mode, a sensor 93 within the decontamination chamber 80 detects levels of sanitizing compound within the decontamination chamber 80 and transmits this data to the controller 86. The controller 86 may be programmed such that once the level of the detected disinfectant compound has dropped to a predetermined threshold for a predetermined time duration, signals are generated to turn off the HVAC system 88. For example, if hydrogen peroxide is the detected compound the threshold concentration may be 1 ppm and the time duration may be 3 minutes. When a decontamination operation of the chamber 80 is completed, the controller 86 touchscreen may be configured to display an amount of disinfectant solution used and an amount of disinfectant solution remaining in the reservoir 85. Although the embodiment of the decontamination module 77 depicted in FIGS. 9A-9B has an internal controller 86, the decontamination module 77 may be controlled by the central controller 73, for example.

Although the storage/decontamination module 77 depicted in FIGS. 9A-9B is used within the portable system 10 to decontaminate components of the aircraft 12 that are not positioned in the enclosure 17, the storage/decontamination module 77 is not limited to this arrangement. In one embodiment, the storage/decontamination module 77 may be an independent novel system that is transported to a location of an aircraft or other transportation asset, and is used to decontaminate components of the aircraft or transportation asset that cannot be decontaminated using bio-thermal decontamination.

Figure 10:
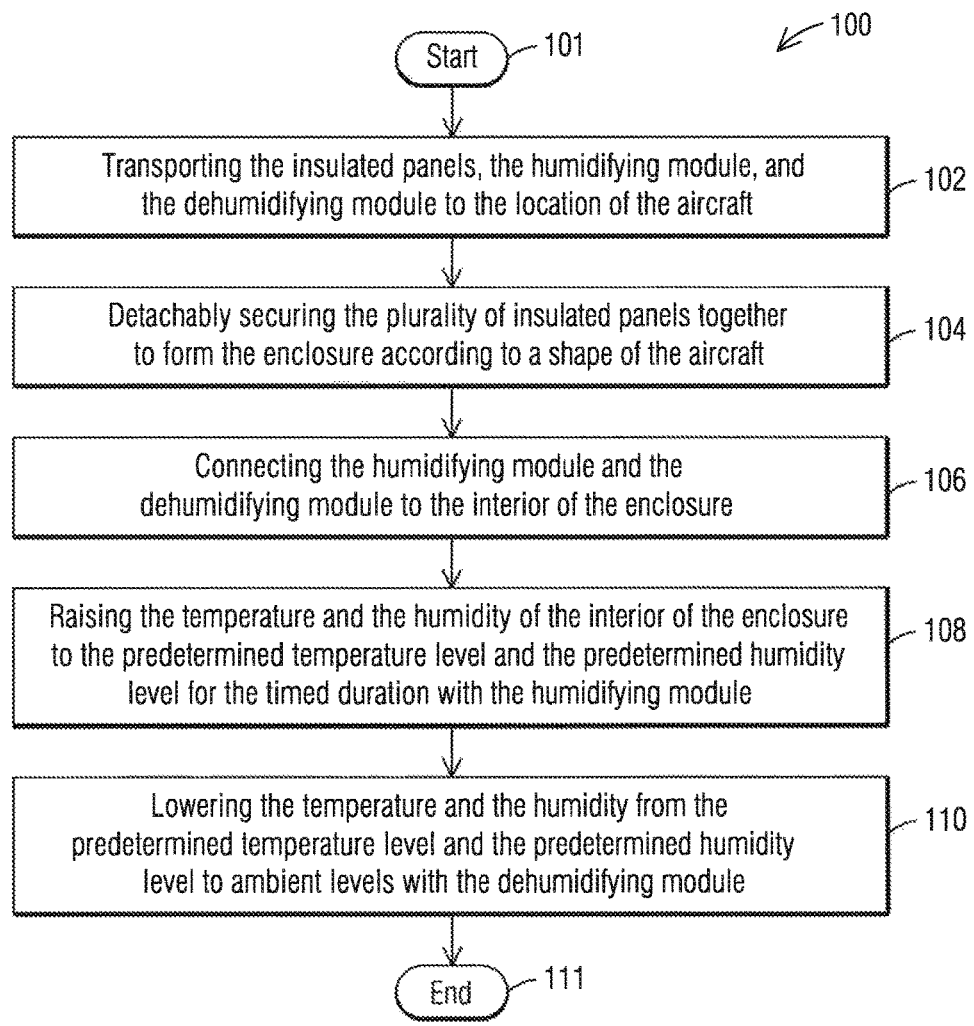
FIG. 10 is a flowchart depicting a method for portable decontamination of a transportation asset.

FIG. 10 illustrates a flowchart depicting a method 100 for portable decontamination of a transportation asset, such as the aircraft 12. The method 100 begins at 101 by transporting 102 the plurality of insulated panels 18, the humidifying module 52 and the dehumidifying module 62 to the location of the aircraft 12. The method 100 also includes detachably securing 104 the plurality of insulated panels 18 together to form the enclosure 17 according to a shape of the aircraft 12. The method 100 also includes connecting 106 the humidifying module 52 and the dehumidifying module 62 in fluid flow communication to the interior 19 of the enclosure 17 and an interior 13 of the aircraft 12. The method 100 also includes raising 108 the temperature and the humidity of the interior 19 of the enclosure 17 and interior 13 of the aircraft 12 to the predetermined temperature level and the predetermined humidity level for the timed duration with the humidifying module 52. The method also includes lowering 110 the temperature and the humidity from the predetermined temperature level and the predetermined humidity level to ambient levels with the dehumidifying module 62, before ending at 111.

While certain embodiments of the present invention have been shown and described herein, such embodiments are provided by way of example only. Numerous variations, changes and substitutions will occur to those of skill in the art without departing from the invention herein. Accordingly, it is intended that the invention be limited only by the spirit and scope of the appended claims.

What is claimed is:
1. A reusable portable decontamination system for a transportation asset, comprising:
    a plurality of insulated panels detachably secured together to form an enclosure with an interior and the enclosure is configured to receive a transportation asset, the enclosure comprising a first opening to the interior and a second opening to the interior;
    a humidifying module externally positioned relative to the interior of the enclosure and in fluid communication with the interior of the enclosure via at least one first insulated duct connected between the humidifying module and the first opening to raise a temperature and a humidity of the interior of the enclosure to a predetermined temperature level and a predetermined humidity level for a timed duration; and
    a dehumidifying module in fluid communication with the interior of the enclosure via at least one second insulated duct connected between the dehumidifying module and the second opening to lower the temperature and the humidity of the interior of the enclosure from the predetermined temperature level and the predetermined humidity level to ambient levels.

2. The reusable portable decontamination system of claim 1, further comprising a storage and decontamination module including:
   a decontamination chamber in which to position one or more components of the transportation asset;
   a reservoir containing a disinfectant solution;
   a pump in fluid communication with the reservoir;
   one or more nozzles in fluid communication with the reservoir and the pump; and
   a programmable controller in signal communication with the pump to activate the pump to deliver the disinfectant solution to the one or more nozzles, wherein the solution is dispersed in atomized form in an interior of the decontamination chamber to decontaminate the one or more components.

3. The reusable portable decontamination system of claim 2, further including a plurality of shelves pivotally mounted to an interior surface of the decontamination chamber, such that at least one shelf of the plurality of shelves can be pivoted to a horizontal position to support the one or more components in the decontamination chamber.

4. The reusable portable decontamination system of claim 1, further comprising:
   one or more sensors positioned within the enclosure interior and an interior of the transportation asset to monitor the temperature and the humidity of the interior of the enclosure and the interior of the transportation asset; and
   one or more controllers in signal communication with the one or more sensors, the humidifying module and the dehumidifying module;
   wherein the one or more controllers are configured to activate the humidifying module to increase the temperature to the predetermined temperature level and the humidity to the predetermined humidity level;
   wherein the one or more controllers are configured to control the humidifying module to maintain the temperature at the predetermined temperature level and the humidity at the predetermined humidity level for the timed duration;
   and wherein upon an elapse of the timed duration, the one or more controller are configured to activate the dehumidifying module to decrease the temperature from the predetermined temperature level and the humidity from the predetermined humidity level to the ambient levels.

5. The reusable portable decontamination system of claim 1, wherein each insulated panel includes a pair of metallic sheets with an insulating foam layer there between.

6. The reusable portable decontamination system of claim 1, wherein the enclosure is formed based on a shape of the transportation asset to define the interior with a minimum clearance between the transportation asset and the enclosure.

7. The reusable portable decontamination system of claim 1, wherein a plurality of insulated ducts extend within the interior of the enclosure including a third insulated duct positioned within a region of the enclosure interior that is external to the transportation asset and a fourth insulated duct positioned within the interior of the transportation asset.

8. The reusable portable decontamination system of claim 7, wherein the second insulated duct includes a plurality of openings along a length of the second insulated duct, to provide fluid flow communication between the humidifying module and the interior of the transportation asset along the length of the second insulated duct.

9. The reusable portable decontamination system of claim 1, wherein the humidifying module comprises:
   a boiler to heat water and generate steam;
   a dispensing coil in fluid communication with the boiler to distribute heat from the steam into air within a chamber,
   a blower in fluid communication with the dispensing coil to push the air from the chamber into an insulated duct; and
   the enclosure interior and an interior of the transportation asset in fluid communication with the blower and the insulated duct to receive the air.

10. The reusable portable decontamination system of claim 9, further comprising one or more sensors to monitor the temperature and the humidity within the enclosure interior and the transportation asset interior, and a controller in communication with the one or more sensors, said controller configured to activate the boiler to increase the temperature and the humidity within the enclosure interior and the transportation asset interior to the predetermined temperature level and the predetermined humidity level.

11. The reusable portable decontamination system of claim 10, further comprising:
   a return insulated duct in fluid communication with the enclosure interior to pass air from the enclosure interior to the chamber within the humidifying module; and
   wherein the controller is configured to selectively activate the boiler to maintain the temperature and the humidity within the enclosure interior and the transportation asset interior at the predetermined temperature level and the predetermined humidity level for the timed duration.

12. A reusable portable decontamination system for a transportation asset, comprising:
   a plurality of insulated panels detachably secured together to form an enclosure with an interior and the enclosure is configured to receive a transportation asset;
   a humidifying module externally positioned relative to the interior of the enclosure and in fluid communication with the interior of the enclosure to raise a temperature and a humidity of the interior of the enclosure to a predetermined temperature level and a predetermined humidity level for a timed duration; and
   a dehumidifying module in fluid communication with the interior of the enclosure to lower the temperature and the humidity of the interior of the enclosure from the predetermined temperature level and the predetermined humidity level to ambient levels;
   wherein the dehumidifying module comprises:
   a chiller to cool water;
   a coil in fluid communication with the chiller to cool air within a chamber; and
   a blower in fluid communication with the coil to push the air from the chamber into an insulated duct; and
   the enclosure interior and an interior of the transportation asset in fluid communication with the blower and the insulated duct to receive the air.

13. The reusable portable decontamination system of claim 12, further comprising a return insulated duct in fluid communication with the enclosure interior to pass air from the enclosure to the chamber in the dehumidifying module.

14. The reusable portable decontamination system of claim 12, further comprising one or more sensors to monitor the temperature and the humidity within the enclosure interior and the transportation asset interior, and one or more controllers in signal communication with the one or more sensors, said one or more controllers being configured to activate the chiller upon elapse of the timed duration to reduce the temperature and the humidity within the enclosure interior and the transportation asset interior from the predetermined temperature level and the predetermined humidity level to the ambient levels.

15. A storage and decontamination module comprising:

a decontamination chamber in which to position one or more components of a transportation asset and a door to the decontamination chamber;

a staging room including a reservoir containing a disinfectant solution;

a pump in the staging room in fluid communication with the reservoir;

a door to the staging room;

one or more nozzles in the decontamination chamber and in fluid communication with the reservoir and the pump;

a programmable controller in the staging room in signal communication with the pump to activate the pump to deliver the disinfectant solution to the one or more nozzles, wherein the solution is dispersed in atomized form in an interior of the decontamination chamber to decontaminate the one or more components; and, a partition in an interior of the module separating the decontamination chamber from the staging room.

16. The storage and decontamination module of claim 15, further comprising a plurality of shelves pivotally mounted to an interior surface of the decontamination chamber, such that at least one shelf of the plurality of shelves can be pivoted to a horizontal position to support the one or more components in the decontamination chamber.

17. A decontamination system for a transportation asset, comprising:

an enclosure having an interior and the enclosure is configured to receive a transportation asset;

a humidifying module positioned externally relative to the interior of the enclosure and in fluid communication with the interior of the enclosure and an interior of the transportation asset to raise a temperature and a humidity of a region of the enclosure interior that is external to the transportation asset to a predetermined temperature level and a predetermined humidity level for a timed duration and to raise a temperature and a humidity of the transportation asset interior to the predetermined temperate level and the predetermined humidity level for the timed duration;

at least one first insulated conduit providing the fluid communication between the humidifying module and the interior of the enclosure via at least one first opening in the enclosure;

a dehumidifying module positioned externally relative to the interior of the enclosure and in fluid communication with the interior of the enclosure and the interior of the transportation asset to lower the temperature and the humidity of the region of the enclosure interior that is external to the transportation asset from the predetermined temperature level and the predetermined humidity level to ambient levels and to lower the temperature and the humidity of the transportation asset interior from the predetermined temperature level and the predetermined humidity level to ambient levels, and at least one second insulated conduit providing the fluid communication between the dehumidifying module and the interior of the enclosure via at least one second opening in the enclosure.

* * * * *